US012773395B2

(12) United States Patent
Delorme et al.

(10) Patent No.: US 12,773,395 B2
(45) Date of Patent: Oct. 27, 2026

(54) O-ACETYLSERINE FOR THE USE THEREOF IN THE PREVENTION AND TREATMENT OF GLUCOSE INTOLERANCE AND THE ASSOCIATED DISEASES

(71) Applicants: INSTITUT NATIONAL DE RECHERCHE POUR L'AGRICULTURE, L'ALIMENTATION ET L'ENVIRONNEMENT, Paris (FR); INSTITUT NATIONAL DES SCIENCES ET INDUSTRIES DU VIVANT ET DE L'ENVIRONNEMENT, Palaiseau (FR); UNIVERSITE PARIS-SACLAY, Gif-sur-Yvette (FR)

(72) Inventors: Christine Delorme, Palaiseau (FR); Véronique Douard, Bures-sur-yvette (FR)

(73) Assignees: INSTITUTE NATIONAL DE RECHERCHE POUR L'AGRICULTURE, L'ALIMENTATION ET L'ENVIRONMENT, Paris (FR); INSTITUT NATIONAL DES SCIENCES ET INDUSTRIES DU VIVANT ET DE L'ENVIRONMENT, Palaiseau (FR); UNIVERSITE PARIS-SACLAY, Gif-sur-Yvette (FR)

( * ) Notice: Subject to any disclaimer, the term of this patent is extended or adjusted under 35 U.S.C. 154(b) by 662 days.

(21) Appl. No.: 18/247,928

(22) PCT Filed: Oct. 7, 2021

(86) PCT No.: PCT/EP2021/077779
§ 371 (c)(1),
(2) Date: Apr. 5, 2023

(87) PCT Pub. No.: WO2022/074154
PCT Pub. Date: Apr. 14, 2022

(65) Prior Publication Data

US 2024/0024274 A1 Jan. 25, 2024

(30) Foreign Application Priority Data

Oct. 7, 2020 (FR) ........................................ 2010231

(51) Int. Cl.
*A61K 31/223* (2006.01)
*A61K 45/06* (2006.01)
*A61P 3/10* (2006.01)

(52) U.S. Cl.
CPC ............ *A61K 31/223* (2013.01); *A61K 45/06* (2013.01); *A61P 3/10* (2018.01)

(58) Field of Classification Search
CPC ........ A61K 31/198; A61K 31/223; A61P 3/10
See application file for complete search history.

(56) References Cited

FOREIGN PATENT DOCUMENTS

| | | | |
|---|---|---|---|
| EP | 1 233 067 A1 | 8/2002 | |
| WO | WO-2018117954 A1 * | 6/2018 | ................ A61P 1/16 |

* cited by examiner

*Primary Examiner* — Sarah Pihonak
(74) *Attorney, Agent, or Firm* — WCF IP

(57) ABSTRACT

The present patent application relates to O-acetylserine, or a salt or derivative thereof, for use in the treatment and/or prevention of glucose intolerance and/or one or more diseases associated with glucose intolerance in an individual. The invention also relates to a composition for use in the treatment and/or prevention of glucose intolerance and/or one or more diseases associated with glucose intolerance in an individual, comprising an O-acetylserine, or a salt or derivative thereof, and a physiologically acceptable vehicle.

16 Claims, 5 Drawing Sheets

O-ACETYLSERINE FOR THE USE THEREOF IN THE PREVENTION AND TREATMENT OF GLUCOSE INTOLERANCE AND THE ASSOCIATED DISEASES

TECHNICAL FIELD

The present invention relates to the field of prevention and/or treatment of metabolic disorders such as glucose intolerance or prediabetes, and also diseases related to glucose intolerance, such as type 2 diabetes.

PRIOR ART

Type 2 diabetes (T2DM) is a disease characterized by chronic hyperglycemia, resulting from the inadequate use of insulin by the body. This disease is generally the consequence of excess weight and physical inactivity, for instance obesity, which develops in response to nutritional and lifestyle changes. Thus, risk factors associated with T2DM are notably: overweight, advanced age, poor diet and excess calories or poor nutrition, physical inactivity, smoking or family history (Vazquez et al. Comparison of body mass index, waist circumference, and waist/hip ratio in predicting incident diabetes: a meta-analysis. Epidemiol Rev 2007; 29: 115-28; Diabetes Prevention Program Research Group. Long-term effects of lifestyle intervention or metformin on diabetes development and microvascular complications over 15-year follow-up: the Diabetes Prevention Program Outcomes Study. Lancet Diabetes Endocrinol 2015; 3: 866-75).

T2DM is the most common diabetes in the world, accounting for 90% of all cases (World Health Organization. 1999. Definition, diagnosis and classification of diabetes mellitus and its complications: report of a WHO consultation. Part 1, Diagnosis and classification of diabetes mellitus). Diabetes is a real public health problem due to its global prevalence, which doubled between 1980 and 2014, rising from 4.7% to 8.5% of the adult population (World Diabetes Report, World Health Organization 2016, ISBN: 9789242565256), the high cost of treatment and its complications. Indeed, in the long term, diabetes can affect the heart, blood vessels, eyes, kidneys and nerves, and increase the risk of heart disease and myocardial infarction. Thus, preventing and treating T2DM, is a highly relevant field of therapeutic investigation with high economic and societal stakes (IDF Diabetes Atlas—8th Edition, 2017).

Nowadays, recommendations for hygienic-dietary measures target prediabetes and, although not widely prescribed, preventive treatments are recommended for people who are at high risk of developing type 2 diabetes. Prediabetes, the early and reversible phase of diabetes, is notably characterized by glucose intolerance.

Glucose intolerance is a risk factor for type 2 diabetes, which develops in the prediabetes phase. Glucose intolerance or prediabetes or intermediate hyperglycemia is a disorder of blood glucose. An individual suffering from glucose tolerance has blood glucose levels that are higher than normal but not high enough to make a diagnosis of diabetes. Glucose intolerance can be characterized by the detection of decreased insulin sensitivity or increased insulin resistance.

Prediabetes is a phase in which it is often still possible to reverse the diabetic tendency so as to return to normal blood glucose levels. This precursor state of type 2 diabetes can be reversed in some cases with exercise and dietary adjustment.

In general, physical activity combined with a balanced diet can lower blood glucose and prevent progression to T2DM. However, the projected increase in type 2 diabetes cases in the coming years suggests that these lifestyle adjustments are insufficient. Thus, it appears that a rebalancing of lifestyle is often unrealistic or insufficient and can be combined with oral medication prescribed to control blood glucose levels. However, these medications are few in number and some are not recommended for children and adolescents who are increasingly developing glucose intolerance. For example, metformin, which is generally used for treating T2DM, may be prescribed. Furthermore, there are contraindications and adverse side effects, such as nausea, vomiting, diarrhea, abdominal pain or appetite loss. These adverse effects are the cause of frequent treatment discontinuations (McGovern et al. *Comparison of medication adherence and persistence in type* 2 *diabetes: A systematic review and meta-analysis*. Diabetes Obesity and Metabolism, 2017, 20(4):1040-1043). Long-term metformin treatment is associated with an increased risk of vitamin B6 and B12 deficiencies, which may be accompanied by neurological complications (Porter et al. *Hyperglycemia and Metformin Use Are Associated With B Vitamin Deficiency and Cognitive Dysfunction in Older Adults*. J. Clin. Endocrinol. Metab., 2019, 104(10): 4837-4847).

Targeting the reversible prediabetic state, and in particular glucose intolerance, at an early stage appears to be essential for preventing its progression to type 2 diabetes.

There is a need for novel compounds or compositions for controlling glucose homeostasis. There is also a need for novel compounds or compositions for targeting glucose intolerance. There is a need for novel compounds or compositions that may be safe for administration to children or adolescents.

There is a need for novel treatments for preventing and/or treating glucose intolerance. There is also a need for novel treatments for preventing and/or treating diseases associated with or resulting from glucose intolerance, notably such as type 2 diabetes. Thus, there is a need for novel compounds or compositions for preventing and/or treating prediabetes.

Thus, there is also a need to prevent and/or treat postprandial hyperglycemia.

There is a need to treat and/or prevent diseases associated with glucose intolerance, in particular type 2 diabetes.

The object of the present invention is to meet all or some of these needs.

DISCLOSURE OF THE INVENTION

The present invention proposes a synthetic metabolite, O-acetylserine, for use in the treatment and/or prevention of glucose intolerance. The present invention also proposes O-acetylserine, for use in the treatment and/or prevention of one or more diseases associated with glucose intolerance, and notably type 2 diabetes.

SUMMARY OF THE INVENTION

The object of the present invention is to propose novel substances for use in a therapeutic method for preventing and/or treating glucose intolerance and/or a disease associated with glucose intolerance in an individual.

Surprisingly, the inventors have observed a protective effect of O-acetylserine (or OAS) on glucose homeostasis. OAS limits the onset of glucose intolerance induced by obesogenic diets (rich in fats or sugars) and which precedes the onset of T2DM. The prevention and treatment of glucose intolerance thus allow the prevention and treatment of T2DM.

Thus, according to a first aspect, the invention relates to O-acetylserine, or a salt or derivative thereof, for use in the treatment and/or prevention of glucose intolerance and/or one or more diseases associated with glucose intolerance in an individual.

In a particular embodiment, the disease associated with glucose intolerance is type 2 diabetes.

In addition, the individual may be overweight or obese.

In a particular embodiment, O-acetylserine is a synthetic metabolite of bacteria, in particular a synthetic metabolite of bacteria of the gut microbiota, more particularly a synthetic metabolite of the bacterial strain *Streptococcus salivarius.*

According to a second aspect, the invention relates to a composition for use in the treatment and/or prevention of glucose intolerance and/or one or more diseases associated with glucose intolerance in an individual, comprising an O-acetylserine, or a salt or derivative thereof, and a physiologically acceptable vehicle.

In a particular embodiment, the disease associated with glucose intolerance is type 2 diabetes.

In addition, the individual may be obese.

According to one embodiment, the O-acetylserine is a synthetic metabolite of bacteria, in particular a synthetic metabolite of bacteria of the intestinal microbiota, more particularly a synthetic metabolite of the bacterial strain *Streptococcus salivarius.*

According to the invention, the composition may be an oral composition, in particular in the form of a powder, granules, a food product, a beverage, a pharmaceutical product, a nutraceutical product, a food additive, a food supplement, a wafer capsule or a gel capsule. In a particular embodiment, the composition also comprises an additional active agent, in particular chosen from metabolites, antioxidants, fish oils, DHA, EPA, vitamins, minerals, phytonutrients, proteins, lipids, probiotics, additional active agents for preventing and/or treating glucose intolerance, and combinations thereof.

The diagram on the right represents the average weight of the epididymal adipose tissue of the mice in each group in grams (y-axes). The groups of mice, from left to right, are indicated on the x-axis: Control; HFD and HFD+OAS. The difference in epididymal adipose tissue weight between the control group and the HFD group or the HFD+OAS group is statistically significant (****$p<0.0001$).

Figure 2:
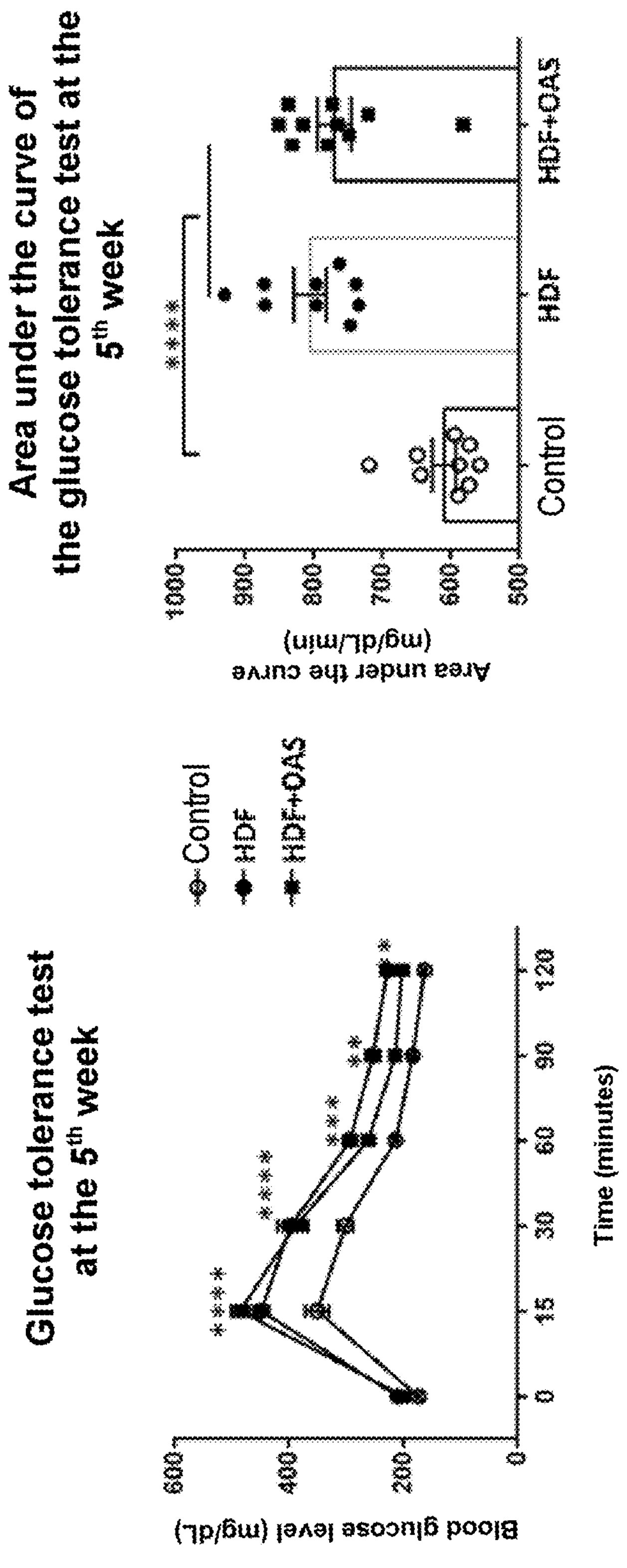

FIG. 2 represents the results of the glucose tolerance test after 5 weeks of study for each of the groups of mice studied: the control group given a control diet, the HFD group given an untreated high-fat diet (HFD), and the HFD group treated with O-acetylserine (HFD+OAS). On the left, the curves represent the change in mean mouse plasma glucose concentration in mg/dl (y-axes) as a function of time in minutes (x-axes) for each group of mice after an oral glucose load. The control group is represented by the curve including the symbol ○, the HFD group is represented by the curve with the symbol ●, and the HFD+OAS group is represented by the curve with the symbol ■. The difference between the control group on the one hand and the HFD and HFD+OAS groups on the other hand is significant (with, respectively **$p<0.0001$, *$p<0.001$, **$p<0.01$, and *$p<0.05$ at t=15 min and at t=30 min, at t=60 min, at t=90 min, and at t=120 min).

On the right, the columns represent the area under the curve in mg/dl/min (y-axes) from the curves in the left diagram for each of the groups of mice indicated, from left to right, on the x-axis: Control; HFD and HFD+OAS. The difference in the area under the curve between the control group on the one hand and the HFD and HFD+OAS groups on the other hand is significant (****$p<0.0001$).

Figure 3:
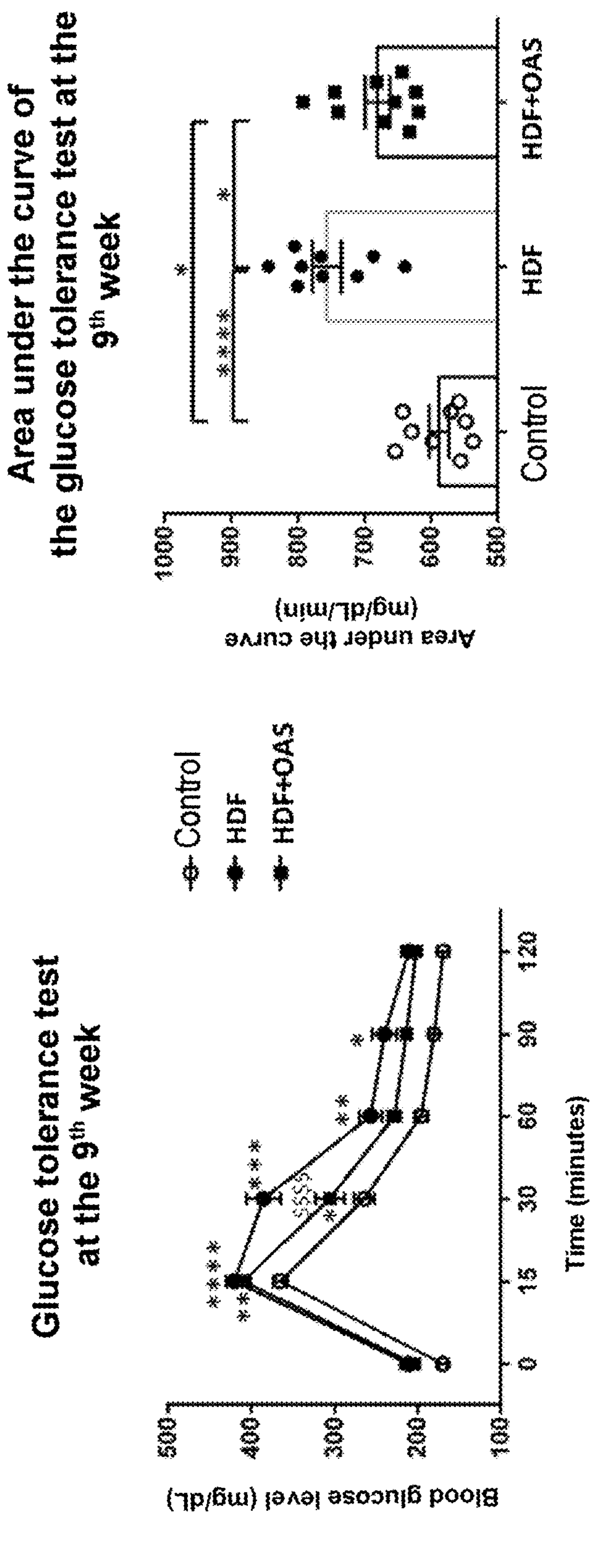

FIG. 3 represents the results of the glucose tolerance test after 9 weeks of study for each of the groups of mice studied: the control group given a control diet, the HFD group given an untreated high-fat diet (HFD), and the HFD group treated with O-acetylserine (HFD+OAS). On the left, the curves represent the change in mean mouse plasma glucose concentration in mg/dl (y-axes) as a function of time in minutes (x-axes) for each group of mice after an oral glucose load. The control group is represented by the curve with the symbol ○, the HFD group is represented by the curve with the symbol ●, and the HFD+OAS group is represented by the curve with the symbol ■. The difference between the control group on the one hand and the HFD and HFD+OAS groups on the other hand is significant (with, respectively **$p<0.0001$, *$p<0.001$, **$p<0.01$, and *$p<0.05$ at t=15 min, at t=30 min, at t=min, and at t=90 min). From t=60 min, the difference between the control group on the one hand and the HFD+OAS group on the other hand is no longer significant and at t=30 min, the difference between the HFD group on the one hand and the HFD+OAS group on the other hand is significant $^{\$\$\$\$}p<0.0001$.

On the right, the columns represent the area under the curve in mg/dl/min (y-axes) from the curves in the left diagram for each of the groups of mice indicated, from left to right, on the x-axis: Control; HFD and HFD+OAS. The difference in the area under the curve between each of the mouse groups is significant (****$p<0.0001$ between the control group and the HFD group, *$p<0.05$ between the HFD group and the HFD+OAS group, and *$p<0.05$ between the control group and the HFD+OAS group).

Figure 4:
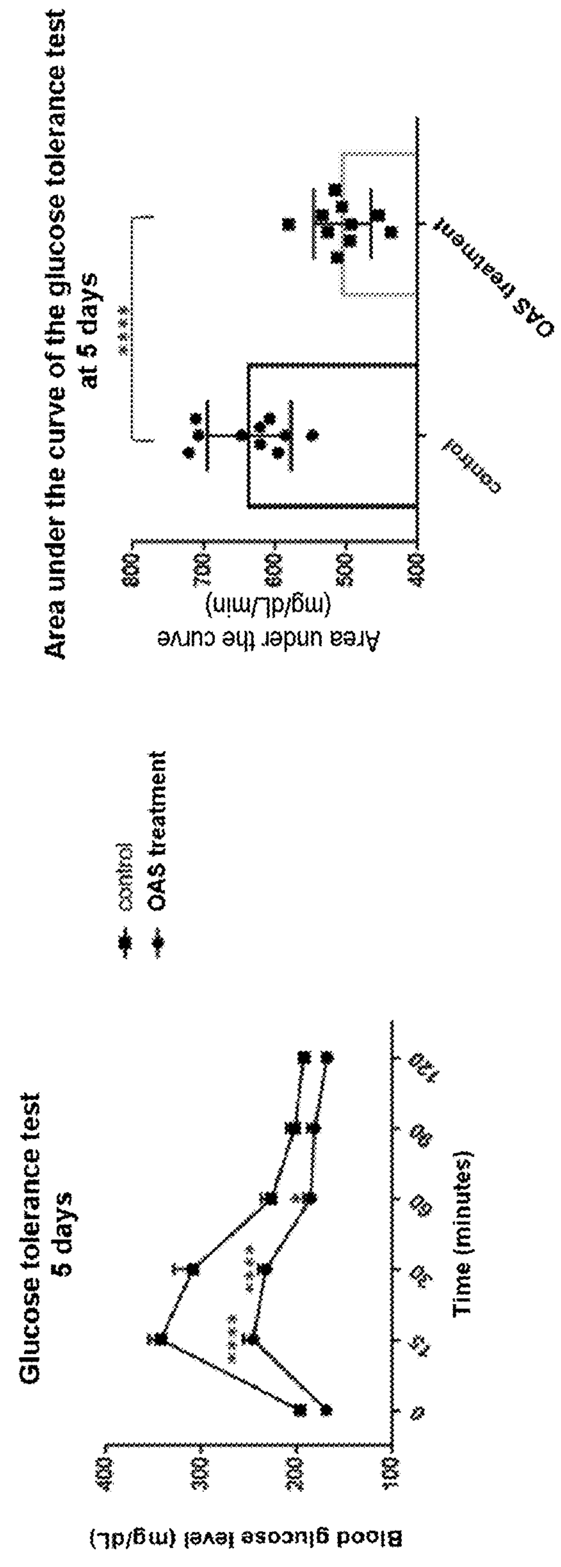

FIG. 4 represents the results of the glucose tolerance test after 5 days of study for each of the groups of mice studied: the control group received a conventional diet and did not receive any O-acetylserine, whereas the OAS group also received a conventional diet plus a daily dose of O-acetylserine (OAS).

On the left, the curves represent the change in mean mouse plasma glucose concentration in mg/dL (y-axes) as a function of time in minutes (x-axes) for each group of mice after an oral glucose load at $t_0$. The control group is represented by the curve with the symbol ■, the OAS group is represented by the curve with the symbol ●. The difference between the control group and the OAS group is significant (with, respectively ****$p<0.0001$ and *$p<0.05$ at t=15 min, at t=30 min, and at t=60 min).

On the right, the columns represent the area under the curve in mg/dL/min (y-axes) from the curves in the left diagram for each of the mouse groups indicated, from left to right, on the x-axis: Control; OAS. The difference in the area under the curve between each of the mouse groups is significant (****$p<0.0001$).

Figure 5:
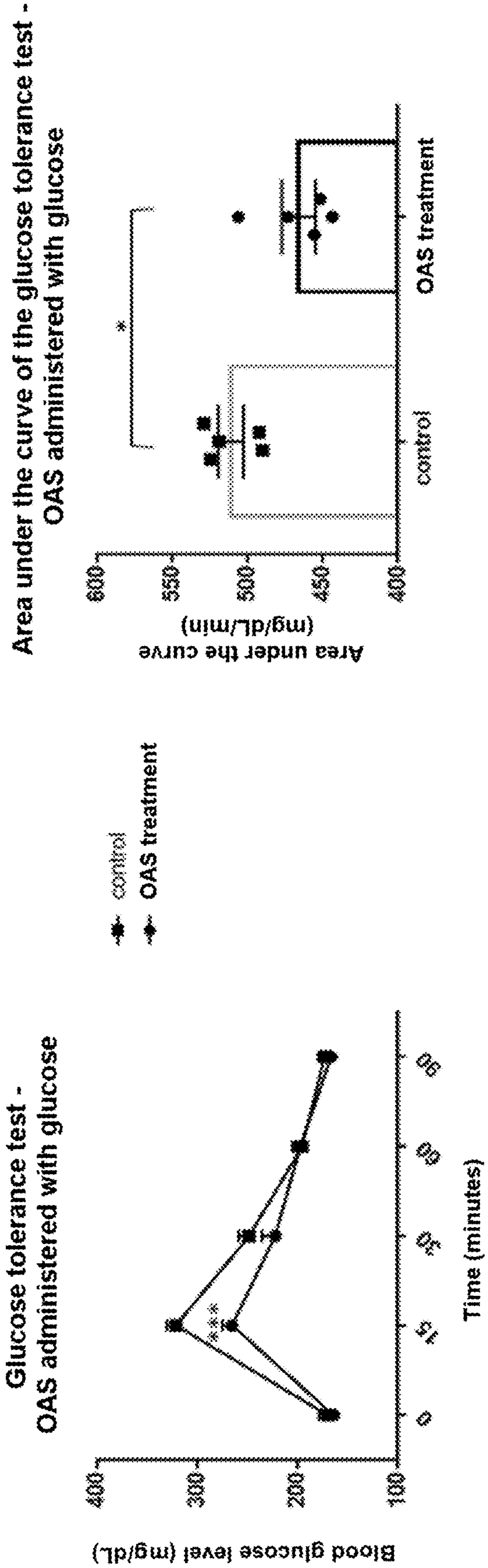

FIG. 5 represents the results of the glucose tolerance test after each group of mice studied received an oral glucose load: the control group received only the oral glucose load at $t_0$, whereas the OAS group received a dose of O-acetylserine (OAS) along with the oral glucose load at $t_0$.

On the left, the curves represent the change in mean mouse plasma glucose concentration in mg/dL (y-axes) as a function of time in minutes (x-axes) for each group of mice after an oral glucose load at $t_0$. The control group is represented by the curve with the symbol ■, the OAS group is represented by the curve with the symbol ●. The difference between the control group and the OAS group is significant (with ***$p<0.001$ at t=15 min).

On the right, the columns represent the area under the curve in mg/dL/min (y-axes) from the curves in the left diagram for each of the mouse groups indicated, from left to right, on the x-axis: Control; OAS. The difference in the area under the curve between each of the mouse groups is significant (*$p<0.05$).

DETAILED DESCRIPTION

The inventors conducted extensive studies to identify the ability of O-acetylserine to treat and/or prevent glucose intolerance and/or a disease associated with glucose intolerance in an individual in need thereof. In particular, the inventors demonstrated the ability of OAS to treat and/or prevent glucose intolerance in mice.

Indeed, as developed in the experimental section below, the inventors demonstrated that treatment with OAS makes it possible to regulate glucose metabolism with, in particular, an improvement in glucose intolerance, in particular glucose intolerance associated with obesity, in a mouse model subjected to an obesogenic diet. They thus demonstrated the usefulness of OAS in improving metabolic disorders in vivo, notably those caused by obesity.

Definitions

The terms used in the present description are used with their usual meaning in the technical field considered, and with regard to the context of the description in which the terms are used. Certain terms are further discussed below, or elsewhere in the description, to provide additional guidance as regards the invention and its implementation. The following definitions are provided for the description and the claims.

The description of the various embodiments of the invention includes embodiments including "comprising", "having", "consisting or" and "consisting essentially or". The words "have" and "comprise", or variants such as "has", "having", "comprises" or "comprising" are to be understood as implying inclusion of the indicated element(s) (such as an element of a composition or a method step) but not the exclusion of other elements. The term "consisting of" implies the inclusion of the element(s) indicated, to the exclusion of any additional element. The term "consisting essentially of" implies the inclusion of the stated elements, and possibly other elements when the other elements do not materially affect the basic and novel features of the invention. Depending on the context, the term "comprise" may also strictly indicate the indicated features, integers, steps, or components, and therefore, in this case, it may be replaced with "consist of".

The term "type 2 diabetes" or "T2DM" refers to a chronic disease that occurs when the pancreas does not produce enough insulin (a hormone that regulates blood sugar levels), or when the body is unable to effectively use the insulin it produces. T2DM is usually preceded by glucose intolerance.

The terms "about" or "approximately" as used herein with regard to a numerical value refer to the usual range of error for the value under consideration, as usually identified by a person skilled in the art under consideration. The mention of the term "about" with regard to a specific value or parameter includes and describes as such that value or parameter. The term "about" refers to ±10% of a given value. However, whenever the value in question refers to an indivisible object that would lose its identity when subdivided, then "about" refers to ±1 of the indivisible object.

The term "individual" or "patient" as used in the present text refers in particular to a mammal. The mammals considered include, but are not limited to, domestic animals (for example cattle, sheep, cats, dogs, and horses), primates (for example human and non-human), rabbits and rodents (for example mice and rats). According to a particular embodiment, an individual, or patient, is a human being.

The term "glucose intolerance" refers to a physiopathological condition in which an individual's blood glucose level is above normal but below the diagnostic threshold for type 2 diabetes. Glucose intolerance can be detected by measuring the fasting blood glucose level and by monitoring blood glucose levels during an oral glucose tolerance test (or OGTT). The term "obesity" refers to a physiopathological state in which an individual notably has an excess of adipose tissue, generally induced by an obesogenic diet, notably including excessive consumption of caloric foods, a genetic predisposition or insufficient or non-existent physical exercise. An individual declared as obese has a body mass index (BMI) greater than 30. The body mass index, according to an official definition by the World Health Organization (WHO), is the indicator of the health risks associated with being overweight or underweight. The BMI is calculated by dividing an individual's weight (in kilograms) by their height (in meters) squared. A BMI value is associated with a specific body type according to the classification given by the WHO.

Unlike an "obese" individual, an "overweight individual" is an individual whose condition is not physiopathological. An overweight individual often also has excess adipose tissue. An individual is generally considered overweight when he or she has a body mass index (BMI) between 25 and 30.

The term "prediabetes" is a physiopathological state notably characterized by a blood glucose level that is high compared to normal, but below the threshold for the definition of type 2 diabetes. A fasting blood glucose level is considered (i) normal between 0.70 and 1.10 g/l, (ii) a sign of prediabetes between 1.10 and 1.25 g/l and (iii) a sign of diabetes when >1.25 g/l. Prediabetes does not usually induce symptoms, but is often associated with obesity, dyslipidemia and hypertension. It is a risk factor for cardiovascular disease. Prediabetes is notably characterized by glucose intolerance.

In the context of the present invention, the terms "prevent", "prevention" and "slow the progression of" (and variants of these terms) with regard to a physiological disorder or disease refers to the prophylactic treatment of the disease or disorder, for example, in an individual suspected of having that disease or disorder, or being at risk of developing that disease or disorder. Prevent includes, but is not limited to, preventing or slowing the development of the disease, and/or maintaining one or more disease symptoms at a desired or lower level. The term "prevent" does not require the 100% elimination of the possibility or likelihood of the disease or disorder occurring. Rather, the term refers to reducing to a lesser degree the risk or probability of occurrence of a given phenomenon, i.e. in the present invention, glucose intolerance or a disease associated with glucose intolerance, such as a prediabetic condition or type 2 diabetes. As noted, prevention may be complete, i.e. the absence of detectable symptoms or disease, or partial, such that there are fewer symptoms or the symptoms are of lesser intensity.

The term "glucose homeostasis" refers to an individual's blood glucose balance which is characteristic of normal blood glucose levels. The normal fasting blood glucose balance in humans is between about 0.70 g/L and about 1.10 g/L (i.e. between 70 mg/dL and 110 mg/dL). A blood glucose level below 0.70 g/L characterizes hypoglycemia, whereas a blood glucose level above 1.10 g/L but below 1.26 g/L characterizes moderate hyperglycemia, which may indicate glucose intolerance.

The term "O-acetylserine salt" means an O-acetylserine salt prepared with physiologically acceptable acids or bases. However, acids or bases that are useful, for example, for the purification or isolation of OAS may also be used. An O-acetylserine salt that may be mentioned is O-acetyl-L-serine hydrochloride.

The term "O-acetylserine derivative" means a physiologically acceptable O-acetylserine which has undergone one or more modifications, such as substitutions or intramolecular migrations. By way of illustration of modification, and in particular substitution, of an O-acetylserine derivative according to the invention, mention may be made of the substitution of at least one of the hydrogens of the amine group of OAS to form an amide function. By way of illustration, a modification, and in particular an additional or alternative substitution, of an O-acetylserine derivative according to the invention may be the substitution of the methyl group of OAS with an alkyl group, in particular with a $(C_1-C_6)$alkyl, the alkyl group being optionally substituted, in particular with a halogen, in particular chosen from F and Cl. By way of illustration, a modification, and in particular an additional or alternative substitution, of an O-acetylserine derivative according to the invention may be the substitution of the proton of the carboxyl group —COOH of OAS to form an ester function. Suitable OAS derivatives according to the invention are OAS compounds which have the same activity, in particular the same activity for preventing and/or treating glucose intolerance and/or a disease associated with glucose intolerance in an individual, as OAS. An O-acetylserine derivative that may be mentioned is N-acetylserine.

As used herein, the terms "therapeutically effective amount" and "prophylactically effective amount" refer to an amount that provides a therapeutic benefit in the treatment, prevention or management of the pathological processes under consideration. The specific amount that is therapeutically effective can be readily determined by a physician and may vary depending on factors such as the type and stage of pathological processes under consideration, the medical history, gender, weight and age of the patient, his or her diet, and the administration of other therapeutic agents.

For the purposes of the invention, the term "significantly" in the context of a change means that the observed change is notable or is statistically significant.

For the purposes of the invention, the terms "substantially similar", "substantially not different", "essentially similar" or "essentially not different" (or any variant thereof) used in connection with a feature of the invention is intended to define a set of embodiments of the invention in connection with that feature that are substantially but not completely identical to embodiments including that feature.

The term "oral glucose tolerance test" or "OGTT test" means a test for measuring the body's ability to utilize glucose. OGTT tests are well known to those skilled in the art. For example, use may be made of the protocol described in Nagy et al., Study of In Vivo Glucose Metabolism in High-fat Diet-fed Mice Using Oral Glucose Tolerance Test (OGTT) and Insulin Tolerance Test (ITT). J. Vis. Exp. (131), e56672, doi:10.3791/56672 (2018).

For the purposes of the invention, the terms "treat", "treatment", "therapy" or "therapeutic" refer to the administration or consumption of an active agent, O-acetylserine or a salt or derivative thereof, or a composition comprising such an active agent for the purpose of curing, alleviating, reducing, attenuating, or amelioration of a disease or pathological disorder, or one or more associated symptoms, or for preventing or slowing the progression of such symptom(s) or disease, or for halting the development of such symptom(s) or disease or pathological disorder in a statistically significant manner. Specifically, the term "treat" or "treatment" includes any approach for obtaining a beneficial effect or desired outcome with regard to a glucose intolerance condition in an individual. Beneficial or desired clinical outcomes may include, but are not limited to, alleviating or improving glucose intolerance, a disease associated with glucose intolerance, such as prediabetes or type 2 diabetes, or one or more symptoms of such a disease; decreasing or reducing the extent of glucose intolerance, a disease associated with glucose intolerance, or one or more symptoms of such a disease; stabilization, i.e. absence of worsening, of glucose intolerance, a disease associated with glucose intolerance, or one or more symptoms of such a disease; prevention of glucose intolerance, a disease associated with glucose intolerance, or one or more symptoms of such a disease; prevention of the spread of a disease associated with glucose intolerance, or one or more symptoms of such a disease; slowing of a disease associated with glucose intolerance, or one or more symptoms of such a disease, or the progression of one or more symptoms of such a disease; reducing the recurrence of glucose intolerance, a disease associated with glucose intolerance, or one or more symptoms of such a disease; and the interruption of glucose intolerance, a disease associated with glucose intolerance, or one or more symptoms of such a disease. In other words, the term "treatment" as used herein includes any cure, improvement, reduction, or interruption of glucose intolerance, a disease associated with glucose intolerance, or one or more symptoms of such a disease. A "reduction" of a symptom or disease means a decrease in the severity or frequency of the disease or symptom, or the elimination of the disease or symptom.

As used in the present description and the claims, the singular forms "a", "an", "one" and "the" include the plurality, unless the context explicitly indicates otherwise.

The term "physiologically acceptable vehicle" is intended to denote any substance or composition that is compatible with the body of the individual to whom an active agent of the invention is to be administered. In particular, a physiologically acceptable vehicle is a substance or composition whose administration to an individual is not accompanied by significant deleterious effects. It may be, for example, a nontoxic solvent such as water or an aqueous saline solution. In particular, such a vehicle is compatible with oral or rectal administration, and is preferably suitable for oral administration.

The list of sources, ingredients and components indicated below are understood to be described such that any combinations and mixtures thereof are also envisaged within the scope of the present invention.

It is understood that each maximum numerical limitation given in the description includes each lower numerical limitation, as if such lower numerical limitations were expressly written. Each minimum numerical limitation given throughout the description includes each higher numerical limitation, as if such higher numerical limitations were expressly written herein. Each numerical range given throughout the description includes each narrower numerical range included within such wider numerical range, as if such narrower numerical ranges were all expressly written.

All the lists given in the description, for instance ingredient lists, are intended to be and should be interpreted as Markush groups. Thus, all the lists can be read and interpreted as elements "selected from the group consisting of" . . . list of elements . . . "and combinations and mixtures thereof".

Reference may be made hereinbelow to trade names of components comprising various ingredients used in the present description. The inventors do not intend to be limited to materials under any particular trade name. Equivalent materials (for example those obtained from a different source under a different name or reference number) to those indicated herein by trade name may be substituted and used in the description below.

O-Acetylserine

The present invention relates to O-acetylserine (OAS), or a salt or derivative thereof, for use in the treatment and/or prevention of glucose intolerance in an individual. The invention also relates to OAS, or a salt or derivative thereof, for use in the treatment and/or prevention of one or more diseases associated with glucose intolerance in an individual.

In particular, the present invention relates to O-acetylserine (OAS), or a salt thereof, or N-acetylserine (NAS), for use in the treatment and/or prevention of glucose intolerance in an individual. The invention also relates to OAS, or a salt thereof, or N-acetylserine (NAS), for use in the treatment and/or prevention of one or more diseases associated with glucose intolerance in an individual.

O-Acetylserine ($C_5H_9NO_4$) is a secondary intracellular metabolite of the metabolism of sulfur-based amino acids of certain bacteria and plants, having the following formula:

TABLE 1

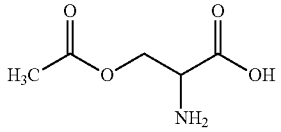

It is a non-proteinogenic α-amino acid derived from serine by acetylation with acetyl-CoA under the influence of serine O-acetyltransferase. It is an intermediate in cysteine biosynthesis in bacteria and plants, which convert it into cysteine by means of cysteine synthase.

The inventors identified OAS in a culture supernatant fraction of a *Streptococcus salivarius* strain by mass spectrometric analyses.

This commensal species is dominantly present in the oral cavity and subdominantly present in the human digestive tract. *S. salivarius* strains are capable of synthesizing OAS.

OAS is also present in various plants.

In humans, this molecule is found in the prostate, urine and blood and is of bacterial origin (notably bacteria of the intestinal microbiota) and food origin.

OAS is referenced as HMDB0003011 in the HMDB 4.0 human metabolite database (hmdb.ca/metabolites/HMDB0003011) and corresponds to CAS number 5147-00-2.

The O-acetylserine according to the invention can also be found as a salt of OAS.

In particular, the OAS may be in the form of O-acetyl-L-serine hydrochloride (OAS·HCl). The salt OAS·HCl ($C_5H_9NO_4 \cdot HCl$) is referenced with the CAS number 66638-22-0.

The O-acetylserine according to the invention may also be in the form of an OAS derivative or in the form of an OAS derivative salt.

In particular, the OAS may be in the form of an N-acetylserine (NAS). The OAS may also be in the form of a salt of NAS.

An OAS that is suitable for use according to the invention is notably sold as a chemical product under the commercial reference A6262_SIGMA® by the company Sigma-Aldrich. An OAS derivative, and in particular N-acetylserine, which is suitable for use according to the invention is notably sold as a chemical product under the commercial reference A2638 ® by the company Sigma-Aldrich.

According to a particular embodiment, the O-acetylserine according to the invention is a synthetic metabolite of bacteria, in particular a synthetic metabolite of bacteria of the intestinal microbiota, more particularly a synthetic metabolite of the bacterial strain *Streptococcus salivarius*.

In certain embodiments, OAS or a salt or derivative thereof may be included in a composition.

Composition

The present invention also relates to a composition for use in the treatment and/or prevention of glucose intolerance and/or one or more diseases associated with glucose intolerance in an individual, comprising O-acetylserine according to the invention, or a salt or derivative thereof, and at least one physiologically acceptable vehicle.

A composition as described is administered to an individual in need thereof in a therapeutically effective amount. This amount is determined based on the characteristics of each individual by medical professionals.

In certain embodiments, the composition is suitable for administration during or outside of meals, preferably outside of a meal. In certain embodiments, the composition may be suitable for administration in at least one daily intake, in particular in a single daily intake. According to certain embodiments, a composition may be administered consecutively each day over the administration period concerned. Alternatively, a composition may be administered over a period of one, two or more consecutive days followed by a period of interruption of at least one, two or more consecutive days. The periods of administration and of interruption may constitute a cycle. A composition may be administered over at least one, and possibly two, three or more consecutive cycles.

A composition may be administered for a period of at least five weeks, or at least six weeks, or at least seven weeks or at least eight weeks, or at least nine weeks.

A composition may be administered for at least two consecutive days, in particular for at least five consecutive days, over a period of one week, and over a period of at least one to at least twelve weeks, in particular from at least one to at least ten weeks, in particular from at least two to at least five weeks, and in particular for at least three weeks.

According to certain embodiments, a composition may be administered for at least two consecutive days over a one-week interval, in particular for at least five consecutive days over a one-week interval.

As physiologically acceptable vehicles that may be used to formulate a composition of the invention, mention may be made, in a nonlimiting manner, of water, saline buffers, notably a phosphate buffer, sodium bicarbonate, juices, dairy products, notably milk or yoghurts, infant food compositions, thickeners such as glyceryl monostearate, sweeteners, coating agents such as rapeseed oil; soybean oil; groundnut oil; soybean lecithin or fish gelatin, diluents such as lactose; lactose monohydrate or starch, binders such as povidone; gelatinized starch; gums; sucrose; polyethylene glycol (PEG) 4000 or PEG 6000, dispersants such as microcrystalline cellulose or sodium carboxymethyl starch, such as sodium carboxymethyl starch type A, lubricants such as magnesium stearate, fluidizing agents such as anhydrous colloidal silica, etc.

A physiologically acceptable vehicle may be any substance used for the preparation of pharmaceutical presentation forms, including coating materials, film-forming materials, fillers, disintegrants, release-modifying materials, support materials, diluents, binders and other adjuvants. Typical physiologically acceptable vehicles include substances such as sucrose, mannitol, sorbitol, starch and starch derivatives, lactose, lubricants such as magnesium stearate, disintegrants, and buffering agents. Also, the suitable physiologically acceptable vehicles include, for example, water, saline solutions, alcohols, oils, preferably plant oils, polyethylene glycols, gelatin, lactose, amylose, magnesium stearate, surfactants, perfume oil, fatty acid, monoglycerides and diglycerides, hydroxymethylcellulose, polyvinylpyrrolidone and the like. The pharmaceutical compositions may comprise auxiliary agents, such as lubricants, preserving agents, stabilizers, wetting agents, emulsifiers, salts for influencing osmotic pressure, buffers, colorants, flavorings and/or aromatic substances. Liquid forms are envisaged for the present invention. These may include emulsions, solutions, suspensions and syrups. Solid forms are also envisaged, such as suppositories, tablets, lozenges, pills, gel capsules, powders, effervescent formulations, dragees, granules, or wafer capsules.

A composition according to the invention may also comprise any additive or excipient usually used in the art with regard to the intended use of the composition. Thus, a composition of the invention may also comprise at least one chosen from a sweetener, a stabilizer, an antioxidant, an additive, a flavoring and/or a colorant. The formulation of a composition of the invention is performed by means of the usual processes used in the field, notably to produce sugar-coated tablets, gel capsules, gels, controlled-release hydrogels, emulsions, foams, syrups, liquids, tablets, wafer capsules or suppositories.

The present composition may be suitable for oral, sublingual, nasal, or rectal administration, particularly oral administration.

In one embodiment, the composition may be in the form of a dietary supplement, a beverage supplement, a nutritional product, a medical food, or a nutraceutical composition.

A composition may also be in the form of a nutritional or nutraceutical composition.

In particular, a composition may be a dietary supplement.

In particular, a dietary supplement may be in the form of wafer capsules, gel capsules, soft capsules, tablets, sugar-coated tablets, pills, pastes, lozenges, gums, drinkable solutions or emulsions, syrups or gels.

A composition that is suitable for use in the invention may notably be formulated in the form of a food supplement chosen from dairy products, dairy drinks, yoghurts, fruit or vegetable juices or their concentrates, powders, soy or cereal-based drinks, breakfast cereals such as muesli flakes, fruit and vegetable juice powders, cereal and/or chocolate bars, confectionery, spreads, milk flours, smoothies, ice creams, reconstituted fruit products, food bars, sauces, sports supplements, including dairy and non-dairy sports supplements, a dessert, a frozen food, a soup, a liquid suspension, a tablet, a gum or a candy.

Advantageously, a composition according to the present invention, intended for oral administration, may be provided with a coating resistant to gastric juice, so as to ensure that the O-acetylserine of the invention included in said composition can pass through the stomach without being damaged. Thus, the release of the OAS according to the invention can take place for the first time in the upper intestinal tract.

According to a particular embodiment, an oral composition that is suitable for use in the invention may be chosen from a powder, granules, a food product, a beverage, a pharmaceutical product, a nutraceutical product, a food additive, a dietary supplement, a wafer capsule or a gel capsule.

In another embodiment of the invention, a composition may be administered rectally. In particular, a rectal composition may be prepared in the form of a suppository, enema or foam.

In one embodiment, a composition may also comprise at least one additional active agent chosen from: metabolites, antioxidants, fish oils, DHA, EPA, vitamins, minerals, phytonutrients, proteins, lipids, probiotics and combinations thereof.

As probiotic active agents that may be used additionally, mention may be made of the strains of probiotic bacteria derived from *Streptococcus, Lactobacillus, Lactococcus, Bifidobacterium, Veillonella, Desemzia, Coprococcus, Collinsella, Citrobacter, Turicibacter, Sutterella, Subdoligranulum, Sporobacter, Sporacetigenium, Ruminococcus, Roseburia, Proteus, Propionobacterium, Leuconostoc, Weissella, Pediococcus, Prevotella, Parabacteroides, Papillibacter, Oscillospira, Melissococcus, Dorea, Dialister, Clostridium, Cedecea, Catenibacterium, Butyrivibrio, Buttiauxella, Bulleidia, Bilophila, Bacteroides, Anaerovorax, Anaerostopes, Anaerofilum, Enterobacteriaceae, Fermicutes, Atopobium, Alistipes, Acinetobacter, Slackie, Shigella, Shewanella, Serratia, Mahella, Lachnospira, Klebsiella, Idiomarina, Fusobacterium, Faecalibacterium, Eubacterium, Enterococcus, Enterobacter* or *Eggerthella.*

As phytonutrients that are suitable for use in the invention, mention may be made of carotenoids, polyphenols or resveratrol. As antioxidants that are suitable for use in the invention, mention may be made of vitamin C, glutathione, caffeine or tocopherol. As vitamins that are suitable for use in the invention, mention may be made of vitamins A, B, C or D. As minerals, mention may be made of iron, magnesium, calcium, zinc, copper or sodium.

In particular, the composition may comprise at least one additional active agent for preventing and/or treating glucose intolerance. Said at least one additional active agent for preventing and/or treating glucose intolerance is different from OAS, or a salt or derivative thereof.

According to one embodiment, a composition according to the invention comprises O-acetylserine, or a salt or derivative thereof, according to the invention, at least one physiologically acceptable vehicle, and at least one additional active agent for preventing and/or treating glucose intolerance.

In particular, the additional active agent may be any antidiabetic molecule and in particular metformin. Glucose intolerance can be treated with an alpha-glucosidase inhibitor (Acarbose, Voglibose), or a pancreatic lipase inhibitor (Orlistat), or a glinide (Nateglinide) or an incretinomimetic (Liraglutide).

Metformin ($C_4H_{11}N_5$) is an oral antidiabetic agent of the normoglycemic biguanide family used in the treatment of type 2 diabetes and recommended for prediabetic people most at risk of developing type 2 diabetes.

According to one aspect, the administration in the same composition of OAS, or a salt or derivative thereof, and metformin makes it possible to reduce the amount of metformin in the composition, compared to a composition comprising only metformin, while at the same time having an equivalent action on the prevention and/or treatment of glucose intolerance and/or a disease associated with glucose intolerance.

According to a particular embodiment, the composition is not a nutritional composition comprising a mixture of oligosaccharides consisting of an N-acetylated oligosaccharide, a galacto-oligosaccharide and a sialylated oligosaccharide.

According to another embodiment, a composition of the invention is not intended to be used for reducing and/or preventing excessive accumulation of body fat in an infant or young child, and/or for the prevention of a health disorder at a later age related to excessive accumulation of body fat in an infant or young child, such as obesity at a later age, and associated comorbidities.

Glucose Intolerance and Associated Diseases

As indicated previously, the OAS according to the invention, or a salt or derivative thereof, or a composition according to the invention, are used in a therapeutic method for preventing and/or treating glucose intolerance and/or one or more diseases associated with glucose intolerance in an individual.

An individual or patient under consideration according to the invention may be a mammal. A mammal toward which the invention is directed may be chosen, for example, from domestic animals (such as cattle, sheep, cats, dogs, and horses, notably cats and dogs), primates, such as human and non-human primates, rabbits, and rodents, such as mice and rats. According to one embodiment, an individual or patient toward whom the invention is directed may be a human being.

OAS or a salt or derivative thereof, or a composition according to the invention, may be particularly suitable for use in a therapeutic treatment for preventing and/or treating prediabetes, and/or a disease or disorder associated with prediabetes, or a symptom of prediabetes.

Glucose intolerance or prediabetes may be asymptomatic. However, they may be associated with obesity, dyslipidemia with a high level of triglycerides and/or a low level of HDL cholesterol, and hypertension. Glucose intolerance and prediabetes are associated with an increased risk of cardiovascular disease. Prediabetes and glucose intolerance are considered an early phase of type 2 diabetes.

Glucose intolerance or prediabetes can be diagnosed by various methods known to those skilled in the art. In particular, glucose intolerance in humans is diagnosed on the basis of two criteria:

the fasting blood glucose level, and the blood glucose level two hours after an oral ingestion of glucose.

Thus, glucose intolerance can be diagnosed if: (i) the fasting blood glucose level is: between 6.1 and 6.9 mmol/L (110-125 mg/dL) and if (ii) two hours after a 75 g oral glucose ingestion, the blood glucose level is between 7.8 mmol/L and 11.0 mmol/L (140 mg/dL to 199 mg/dL). Measurement of the blood glucose level two hours after glucose ingestion is performed by an oral glucose tolerance test or OGTT. Such a test is described in Hjellestad et al., *HbA1c versus oral glucose tolerance test as a method to diagnose diabetes mellitus in vascular surgery patients*, Cardiovascular Diabetology, 12:79 (2013).

Glucose intolerance or prediabetes can usually be followed by type 2 diabetes. Type 2 diabetes (or T2DM) is a disease associated with glucose intolerance or prediabetes. According to one embodiment, OAS or a salt or derivative thereof or a composition according to the invention may be particularly suitable for use in a therapeutic treatment for preventing and/or treating type 2 diabetes.

A T2DM can be diagnosed by various methods known to those skilled in the art. In particular, a T2DM can be diagnosed if one or more from among the following criteria are met:

fasting blood glucose level, blood glucose level two hours after oral ingestion of glucose, or postprandial or random blood glucose level glycated hemoglobin A1C (HbA1C).

Thus, T2DM is diagnosed if the blood glucose levels are: (i) fasting, greater than or equal to a 7.0 mmol/L (126 mg/dL), or if (ii) two hours after a 75 g oral glucose ingestion, greater than or equal to 11.1 mmol/L (200 mg/dL), or if (iii) the random plasma glucose level is greater than 11.1 mmol/L (200 mg/dL), or if (iv) glycated hemoglobin A1c (HbA1c) is greater than or equal to 48 mmol/mol (equivalent to 6.5%).

According to one embodiment, the present invention also relates to a therapeutic treatment method for preventing and/or treating glucose intolerance and/or a disease associated with glucose intolerance in an individual in need thereof, comprising at least one step of administering to said individual OAS or a salt or derivative thereof or administering to said individual a composition according to the invention.

According to one embodiment, the present invention also relates to a therapeutic treatment method for preventing and/or treating prediabetes and/or a disease associated with prediabetes in an individual in need thereof, comprising at least one step of administering to said individual OAS or a salt or derivative thereof, or administering to said individual a composition according to the invention.

According to one embodiment, the present invention also relates to a therapeutic treatment method for preventing and/or treating type 2 diabetes in an individual in need thereof, comprising at least one step of administering to said individual OAS or a salt or derivative thereof, or administering to said individual a composition according to the invention.

A method according to the invention may comprise, prior to the step of administering an active agent of the invention, a step of diagnosing glucose intolerance, prediabetes or type 2 diabetes. Such a diagnosis may be made by any diagnostic method known to those skilled in the art for this purpose, and notably via one of the methods described above.

A method according to the invention may also comprise a step of observing the reduction, suppression, or improvement of a symptom or glycemic marker of glucose intolerance, prediabetes or type 2 diabetes.

According to a particular embodiment, an individual or patient under consideration for the invention may be overweight or obese.

A use or method according to the invention may comprise administering to an individual or patient in need thereof. OAS or a salt or derivative thereof, or a composition according to the invention via any suitable route of administration. Examples that may be mentioned include include oral, sublingual, nasal, or rectal administration. Preferably, an administration of OAS or a salt or derivative thereof, or of a composition according to the invention may be performed orally.

According to one embodiment, OAS or a salt or derivative thereof or the composition according to the invention may be administered in at least one daily dose, in particular two or three daily doses, more particularly in at least one daily dose.

The intake of OAS or a salt or derivative thereof or the composition according to the invention may be taken at the time of a meal, or outside of meals. Over a 24-hour period, OAS or a salt or derivative thereof or a composition according to the invention may be taken at any time. In particular, OAS or a salt or derivative thereof or a composition according to the invention may be taken in the morning, and in particular at the time of the morning meal. In particular, the administration of OAS or a salt or derivative thereof or of a composition according to the invention may be performed outside of meals, notably in one daily intake. The period of time during which OAS or a salt or derivative thereof or a composition according to the invention is administered depends on several factors, such as the age, weight and gender of the patient, the presence of other pathological disorders, and the diet, and is adapted by a person skilled in the art according to the usual practice in the field.

A suitable period of time for administration of OAS or a salt or derivative thereof or a composition according to the invention may be at least five weeks, or at least six weeks, or at least seven weeks or at least eight weeks, or at least nine weeks.

During a period of administration, OAS or a salt or derivative thereof or the composition according to the invention may be administered consecutively every day, or the administration may be performed in periods of one or more days, followed by an interruption period of one or more days, where applicable followed by one or more cycles of administration and interruption.

According to certain embodiments, OAS or a salt or derivative thereof or the composition according to the invention may be administered over a period of one, two or more consecutive days followed by an interruption period of at least one, two or more consecutive days. The periods of administration and of interruption may constitute a cycle. The administration of OAS or a salt or derivative thereof or a composition according to the invention may be performed over at least one, or even two, three or more consecutive cycles. Thus, OAS or a salt or derivative thereof or the composition according to the invention may be administered for at least two consecutive days over a one-week interval. According to one embodiment, the administration may be performed for at least five consecutive days over a one-week interval. The administration may be continued over two, three or more weeks as described above.

According to one embodiment, OAS or a salt or derivative thereof or the composition according to the invention may be administered in a therapeutically effective amount or dose. In particular, OAS or a salt or derivative thereof or the composition according to the invention may be administered in a daily dose equivalent to a dose ranging from at least about 70 mg/kg/d to at least about 2000 mg/kg/d. In particular, a dose that is suitable for use in the invention may be from at least about 100 mg/kg/d to at least about 1000 mg/kg/d, and in particular from at least about 200 mg/kg/d to at least about 500 mg/kg/d.

According to another aspect, the invention also relates to the use of OAS or a salt or derivative thereof or the composition according to the invention for the manufacture of a medicament. In particular, the invention relates to the use of OAS or a salt or derivative thereof or the composition according to the invention for the manufacture of a medicament for preventing and/or treating glucose intolerance and/or one or more diseases associated with glucose intolerance.

It is understood that the invention encompasses all the variations, combinations and permutations in which one or more limitations, elements, clauses, descriptive terms, etc., of one or more of the claims listed below may be introduced into another claim dependent on the same basic claim (or, as the case may be, any other claim), unless otherwise indicated or unless it is obvious to those skilled in the art that a contradiction or inconsistency would occur. When items are presented in list form (for example in the Markush group or a similar format), it should be understood that each subgroup of items is also disclosed, and any item may be deleted from the group. It should be understood that in general, when the invention or aspects of the invention is/are designated as comprising particular elements, features, etc., certain embodiments of the invention or aspects of the invention consist of, or consist essentially of, such elements, features, etc. For simplicity, these embodiments have not always been specifically stated in as many words. It should also be understood that any embodiment or aspect of the invention may be explicitly excluded from the claims, irrespective of whether the specific exclusion is mentioned in the specification. Publications and other documents cited to describe the background of the invention and to provide additional details regarding its implementation are incorporated herein by reference. The invention is described in greater detail with the aid of the examples that follow, which are given purely for illustrative purposes, and are not intended to limit the invention.

The invention is described below in greater detail with the aid of the following examples which are given purely for illustrative purposes.

EXAMPLES

Example 1: Preventive Action of a Treatment Based on an Active Agent According to the Invention on Healthy Individuals Male C57BL/6JRj mice aged 7 weeks from Janvier Labs were fed with a conventional diet used in pet shops.

A first group of 10 mice, not treated with OAS, served as a control group.

A second group of 10 mice was treated with a daily dose of OAS at 1000 mg/kg for 5 days.

The OAS used was the product sold under the name A6262_SIGMA by the company Sigma-Aldrich (CAS No. 66638-22-0). This group is the OAS treatment group.

An oral glucose tolerance test (OGTT) was performed on each of the two groups of mice. This test consists of monitoring the plasma glucose concentrations for 120 min, after the mice have received an oral glucose load. Thus, at $T_0$ (fasting blood glucose level), glucose (2.5 g/kg) is given orally to the animal. A drop of blood is taken from the tail every 15 to 30 minutes for 90 minutes to measure the blood glucose level with a strip glucose meter (Accu-Check Perfoma, available in pharmacies).

The OGTT was performed on the fifth day of treatment 2 h after the OAS treatment group received a dose of 500 mg/kg. At the time of the OGTT, the mice of the treatment group also received 500 mg/kg of OAS along with the oral glucose load.

The control group received only the oral glucose load.

The fasting blood glucose levels of the animals tended to be lower in the OAS treatment group and the blood glucose levels at 15 min, 30 min and 60 min after the oral glucose load were significantly lower in the OAS treatment group compared to the control group.

The results of this test show that a 5-day OAS treatment decreases the fasting blood glucose level of the treatment group and significantly decreases the hyperglycemia induced by an oral glucose load (FIG. 4).

This treatment significantly decreases hyperglycemia with an area under the curve lower than that of the control group (FIG. 4), demonstrating the effect of O-acetylserine on regulating postprandial hyperglycemia and thus the preventive action of an active agent according to the invention in the establishment of insulin resistance and/or prediabetes.

Example 2: Preventive Action of a Single Dose of an Active Agent According to the Invention on Postprandial Glycemia in Healthy Individuals Male C57BL/6JRj mice aged 7 weeks from Janvier Labs were fed with a conventional diet used in pet shops.

A first group of 5 mice, not treated with OAS, served as a control group.

A second group of 5 mice was treated with a single dose of OAS at 1000 mg/kg. The OAS used was the product sold under the name A6262 SIGMA by the company Sigma-Aldrich (CAS No. 66638-22-0). This group is the OAS treatment group.

An oral glucose tolerance test (OGTT) was performed on each of the two groups of mice. This test consists of monitoring the plasma glucose concentrations for 120 min, after the mice have received an oral glucose load. Thus, at $T_0$ (fasting blood glucose level), glucose (2.5 g/kg) is given orally to the animal. A drop of blood is taken from the tail every 30 minutes for 120 minutes so as to measure the blood glucose level with a strip glucose meter (Accu-Check Perfoma, available in pharmacies).

In the OGTT test, the OAS treatment group received a dose of 1000 mg/kg of OAS along with the oral glucose load. The control group received only the oral glucose load. The blood glucose levels at 15 min after the oral glucose load were significantly lower in the OAS treatment group compared to the control group.

The results of this test show that after 15 minutes, a single dose of OAS significantly decreases the hyperglycemia induced by an oral glucose load (FIG. 5). This treatment significantly decreases hyperglycemia with a lower area under the curve than the control group (FIG. 5). A single dose of O-acetylserine is able to decrease postprandial hyperglycemia. This thus demonstrates the preventive action of a single dose of an active agent according to the invention in the establishment of insulin resistance and/or prediabetes.

Example 3: Action of the Active Agent According to the Invention on HFD Individuals The action of an active agent according to the invention was also tested in individuals on an obesogenic diet.

Male C57BL/6JRj mice aged 7 weeks from Janvier Labs were fed a high fat diet (HFD, 45% fat and 20% sucrose) for 12 weeks. This diet is comparable to an obesogenic diet that promotes glucose intolerance.

A first group of 10 mice fed this diet was treated with a daily dose of OAS of 200 mg/kg/d, at a frequency of 5 days per week during the 12 weeks of diet. The OAS used was the product sold as A6262_SIGMA by Sigma-Aldrich (CAS No. 66638-22-0). This group is the HFD+OAS group.

The second group of 9 mice fed an HFD diet did not receive any OAS treatment. This is the HFD group.

A final group of 9 mice, which did not receive any particular diet or OAS treatment, served as the control group.

Figure 1:
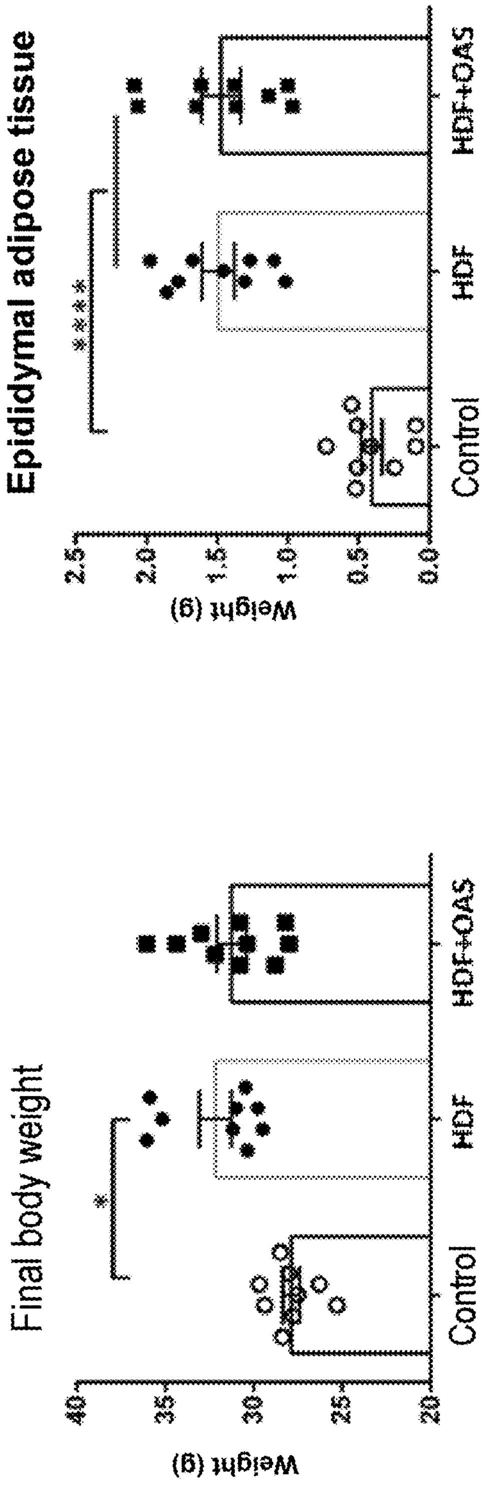
FIG. 1 represents the final body weight (left) and the epididymal adipose tissue weight of the groups of mice studied after 12 weeks of diet and treatment: the control group which received a control diet, the HFD group which received an untreated high-fat diet (HFD), and the HFD group treated with O-acetylserine (HFD+OAS). The diagram on the left represents the average weight of the mice in each group in grams (y-axes). The groups of mice, from left to right, are indicated on the x-axis: Control; HFD and HFD+OAS. The difference in weight between the control group and the HFD group is statistically significant (*$p<0.05$).

In the mice on the HFD diet, a significantly higher weight gain (*$p<0.05$) and a significant increase in adiposity in the epididymis of the mice (**$p<0.0001$) were observed after 12 weeks on the diet, compared with mice not fed an HFD diet (control group). These features are indicative of an establishment of obesity in the mice (FIG. 1**).

An oral glucose tolerance test (OGTT) was performed on each of the three groups of mice. This test consists of monitoring the plasma glucose concentrations for 120 min, after the mice have received an oral glucose load. Thus, at $T_0$ (fasting blood glucose), glucose (2 g/kg) is given orally to the animal. A drop of blood is taken from the tail every 30 minutes for 120 minutes so as to measure the blood glucose level with a strip glucose meter (Accu-Check Perfoma, available in pharmacies).

Glucose tolerance is a reflection of the body's ability to regulate the return to a normal blood glucose level after a glucose load.

The OGTT was performed at 5 weeks and 9 weeks after the start of the obesogenic diet. The results of this test show the installation of glucose intolerance as early as 5 weeks in the groups of mice on the HFD diet. Treatment with OAS had no visible effect in the HFD+OAS group after 5 weeks (FIG. 2). However, after 9 weeks, this treatment significantly decreases glucose intolerance with an area under the curve similar to that of the control group (FIG. 3).

In conclusion, treatment with O-acetylserine makes it possible to regulate glucose metabolism in vivo with an improvement notably in glucose intolerance associated with an obesogenic diet.

The invention claimed is:

1. A method of treating and/or preventing glucose intolerance and/or one or more diseases associated with glucose intolerance comprising providing O-Acetylserine, or a salt thereof to an individual in need thereof.

2. The method claimed in claim 1, in which the disease associated with glucose intolerance is type 2 diabetes.

3. The method claimed in claim 1 in which the individual is overweight or obese.

4. The method as claimed in claim 1 in which the O-acetylserine is a metabolite synthesized by bacteria, a metabolite synthesized by plants or is produced by chemical synthesis.

5. A method of treating and/or preventing glucose intolerance and/or one or more diseases associated with glucose intolerance comprising providing an individual in need thereof a composition comprising an O-acetylserine, or a salt thereof, and a physiologically acceptable vehicle.

6. The method as claimed in claim 5, in which the disease associated with glucose intolerance is type 2 diabetes.

7. The method as claimed in claim 5 in which the individual is obese.

8. The method as claimed in claim 5 in which the O-acetylserine is a metabolite synthesized by bacteria, a metabolite synthesized by plants or is produced by chemical synthesis.

9. The method as claimed in claim 5 in which the composition is an oral composition.

10. The method as claimed in claim 5 in which the composition further comprises an additional active agent.

11. The method of claim 4 wherein the bacteria is bacteria of the intestinal microbiota.

12. The method of claim 4 wherein the bacteria is the bacterial strain *Streptococcus salivarius.*

13. The method of claim 8 wherein the bacteria is bacteria of the intestinal microbiota.

14. The method of claim 8 wherein the bacteria is the bacterial strain *Streptococcus salivarius.*

15. The method of claim 9 wherein the oral composition is selected from the group consisting of a powder, granules, a food product, a beverage, a pharmaceutical product, a nutraceutical product, a food additive, a food supplement, a wafer capsule, and a gel capsule.

16. The method of claim 10 wherein the additional active agent is selected from the group consisting of metabolites, antioxidants, fish oils, DHA, EPA, vitamins, minerals, phytonutrients, proteins, lipids, probiotics, additional active agents for preventing and/or treating glucose intolerance, and combinations thereof.

* * * * *